United States Patent
Ackerman

(10) Patent No.: US 11,872,106 B2
(45) Date of Patent: Jan. 16, 2024

(54) DEVICE AND METHOD FOR CONTROLLING FECAL INCONTINENCE

(71) Applicant: ForConti Medical Ltd., Migdal Haemek (IL)

(72) Inventor: Haim Ackerman, Caesarea (IL)

(73) Assignee: FORCONTI MEDICAL LTD., Migdal Haemek (IL)

( * ) Notice: Subject to any disclaimer, the term of this patent is extended or adjusted under 35 U.S.C. 154(b) by 485 days.

(21) Appl. No.: 16/963,982

(22) PCT Filed: Jan. 15, 2019

(86) PCT No.: PCT/IL2019/050054
§ 371 (c)(1),
(2) Date: Jul. 22, 2020

(87) PCT Pub. No.: WO2019/145937
PCT Pub. Date: Aug. 1, 2019

(65) Prior Publication Data
US 2021/0378810 A1  Dec. 9, 2021

Related U.S. Application Data

(60) Provisional application No. 62/621,070, filed on Jan. 24, 2018.

(51) Int. Cl.
*A61F 2/00* (2006.01)

(52) U.S. Cl.
CPC .... *A61F 2/0013* (2013.01); *A61F 2210/0076* (2013.01); *A61F 2220/0008* (2013.01)

(58) Field of Classification Search
CPC .......... A61F 2/004–0027; A61F 2/0009; A61F 2/0013; A61F 2/0004; A61F 2/0022; A61F 2250/0059; A61F 2250/0003
See application file for complete search history.

(56) References Cited

U.S. PATENT DOCUMENTS

| 4,813,422 A | 3/1989 | Fisher et al. |
| 6,843,766 B1 | 1/2005 | Nemir et al. |
| 2009/0149880 A1* | 6/2009 | Gobel ................... A61F 2/0013 606/192 |
| 2011/0172694 A1* | 7/2011 | Ackerman ............ A61F 2/0009 606/192 |

FOREIGN PATENT DOCUMENTS

IL  210534  5/2017

OTHER PUBLICATIONS

International Search Report of PCT Application No. PCT/IL2019/050054 dated Apr. 16, 2019.

* cited by examiner

*Primary Examiner* — Samuel G Gilbert
(74) *Attorney, Agent, or Firm* — PEARL COHEN ZEDEK LATZER BARATZ LLP

(57) ABSTRACT

This invention is directed to a device and a method for controlling fecal incontinence. The device of this invention is easily inserted into the rectum, and is designed for remaining where required in the rectum, above the dentate line and hemorrhoidal vein area, despite the peristaltic movements of the intestine.

16 Claims, 10 Drawing Sheets

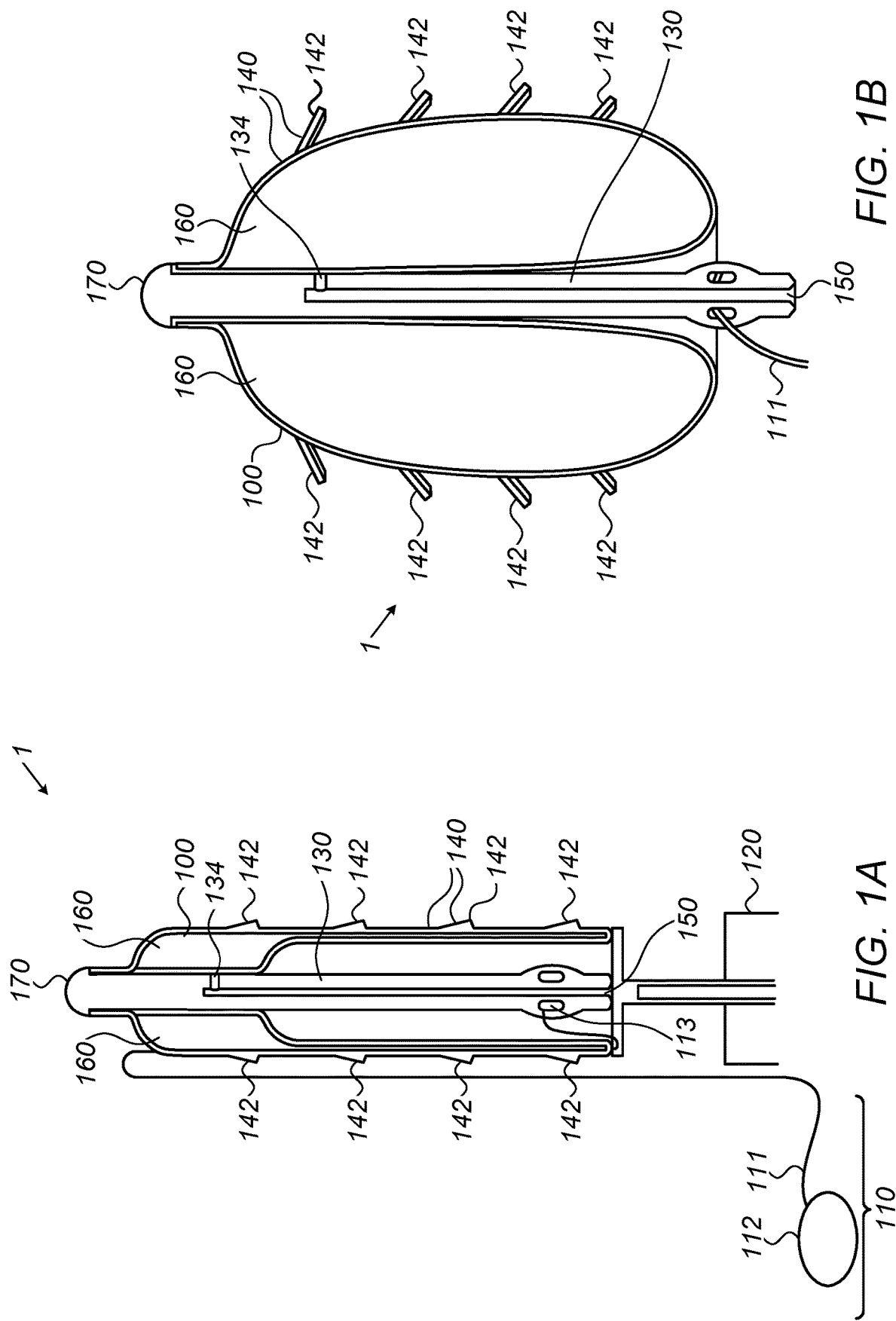

DEVICE AND METHOD FOR CONTROLLING FECAL INCONTINENCE

CROSS-REFERENCE TO RELATED APPLICATIONS

This application is a National Phase Application of PCT International Application No. PCT/IL2019/050054, International Filing Date Jan. 15, 2019, entitled "Device and Method for Controlling Fecal Incontinence", published on Aug. 1, 2019 as International Patent Application Publication No. WO 2019/145937, claiming the benefit of U.S. Provisional Patent Application No. 62/621,070, filed Jan. 24, 2018, which is incorporated herein by reference in its entirety.

FIELD OF THE INVENTION

This invention is directed to a device and a method for controlling fecal incontinence. The device of this invention is easily inserted into the rectum, and is designed for remaining where required in the rectum, above the dentate line, despite the peristaltic movements of the intestine.

BACKGROUND OF THE INVENTION

Fecal incontinence is the impaired ability to control bowel movements. Many patients with fecal incontinence have little or no control over their bowel movements, causing distress and embarrassment and limiting the social activity of the patient. In some patients, particularly older ones, fecal incontinence can cause additional problems such as bed sores, which may lead to gangrene, which may, in turn, result in death. Fecal incontinence is a condition that requires substantial time and labor on part of many health care personnel in hospitals and nursing homes, as well as on the part of the family members of the suffering patient.

Several approaches have been used in order to treat, or at least care for, fecal incontinence. The most simple and common method, which does not actually treat the fecal incontinence but which rather treats the consequences thereof, is the use of an absorbent, such as a diaper. However, diapers are not comfortable to wear, cannot be conveniently used in public, and further, may cause bedsores, mainly in older patients. Other treatments include invasive surgery, which is considered to be a relatively dangerous procedure that cannot be used on all patients, especially if they are suffering from additional conditions or are at an age where invasive surgery may be life threatening.

U.S. Pat. No. 4,813,422 (Fisher et al.) discloses a bowel probe and method for controlling bowel incontinence. The disclosed probe comprises a catheter with an infrared sensor tip, used for sensing fecal mass in the rectum, and a cuff that is inflated to prevent passage of the rectal mass.

However, although previously disclosed devices and methods have, to an extent, been successful in managing incontinence, they are not always reliable or conveniently used. Further, many of the disclosed methods, such as the use of tampon-like devices, create lateral pressure on the rectal wall, which may be both dangerous and painful. Additionally, the rectum includes two regions, separated by what is known by the dentate line. Generally, the region below the dentate line is highly innervated and, therefore, the presence of a device in that area is painful. The peristaltic movements of the intestines tend to push out anything found within the intestines, and, therefore, they are pushed out of the patient's body, thus being ineffective.

Therefore, there is a need in the art for a non-invasive, reliable device and method for treating fecal incontinence without causing pain or damage to the patient.

SUMMARY OF THE INVENTION

Embodiments of the invention are directed to a fecal incontinence controlling device comprising
an inflatable body comprising
a core;
an outer surface; and
a port;
inflating means attached to the port;
deflating means attached to the inflatable body; and
withdrawal means attached to the inflatable body,
wherein any one of the inflating mean and the deflating means may be attached or detached from the port; wherein the withdrawal means may be attached or detailed from the inflatable body; and
wherein the inflatable body has an inflated configuration and a deflated configuration and wherein, in the inflated configuration, the outer surface is corrugated, fluted, grooved, furrowed or comprises puckers or protrusions, such that, when subject to peristaltic movements, the body in the inflated configuration remains about in place in the rectum or moves upwards due to peristalsis, rather than moving naturally downwards.

According to some embodiments, the outer surface is prepared from a single layer. According to some embodiments, the outer surface comprises more than one region, wherein each region is prepared from a different number of layers.

According to some embodiments, the withdrawal means is a tether connected at one end to the inflatable body and, optionally, at the other end to a handle. According to some embodiments, the inflating means is a syringe. According to some embodiments, the deflating means is a syringe. According to some embodiments, the deflating means is a tether connected at one end to the inflatable body and, optionally, at the other end to a handle. According to some embodiments, any two or all of the withdrawal means, inflating means and deflating means are incorporated into a single element. According to some embodiments, the deflating means is attached to the port.

Further embodiments of the invention are directed to a method for controlling fecal incontinence in a patient, the method comprising:
inserting an inflatable body in a deflated configuration into the rectum until reaching a position above the dentate line, wherein the inflatable body comprises comprising a core, an outer surface, and a port;
inflating the inflatable body by inflating means attached to the port thereby transforming the inflatable body to the inflated configuration to provide an inflated body;
detaching the inflating means from the port; and, when desired or required to remove the inflated body from the rectum, if not already attached, attaching deflating means to the inflated body,
deflating the inflated body by the deflating means, thereby transforming the inflatable body to the deflated configuration to provide a deflated body;
if not already attached, attaching withdrawal means to the deflated body;
withdrawing the deflated body from the rectum by withdrawal means.

According to some embodiments, the inflatable body is inflated with air. According to some embodiments, the inflating means is a syringe. According to some embodiments, the deflating means is a syringe. According to some embodiments, the deflating means is a tether, which, when pulled on, causes the inflated body to be transformed to its deflated configuration. According to some embodiments, the withdrawal means is a tether, which, when pulled on, withdraws the deflated body from the rectum. According to some embodiments, the withdrawal means further includes a handle attached to the tether.

BRIEF DESCRIPTION OF THE DRAWINGS

Embodiments of the invention will be understood and appreciated more fully from the following detailed description in conjunction with the figures, which are not to scale, in which like reference numerals indicate corresponding, analogous or similar elements, and in which:

FIG. 1A presents a cross section of an embodiment of the device in the deflated from, whereas FIG. 1B presents a cross section of an embodiment of the device is the inflated form;

DETAILED DESCRIPTION OF THE PRESENT INVENTION

Figure 2A:
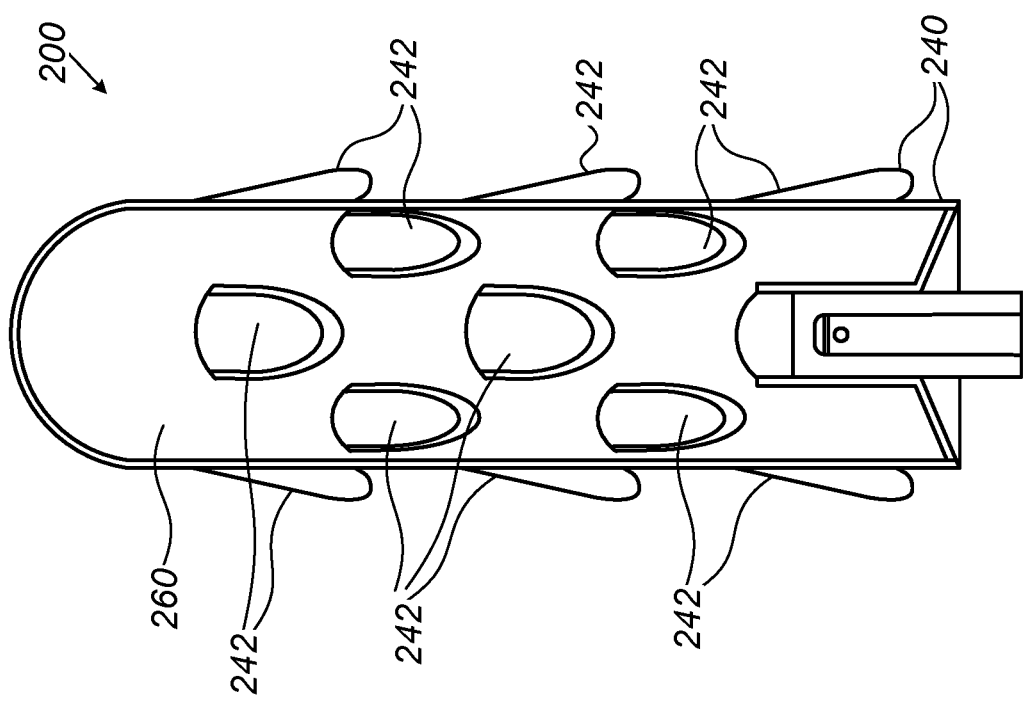
FIGS. 2A and 2B present cross sections of deflated (2A) and inflated (2B) embodiments of bodies of the device comprising inflatable protrusions and FIG. 2C presents a three dimensional inflated form of the same body with inflatable protrusions, wherein the body is prepared from one layer.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Throughout this description, the term "about" is intended to cover ±10% of the specifically disclosed value.

Embodiments of the invention are directed to a fecal incontinence controlling device comprising
an inflatable body comprising
a core;
an outer surface; and
a port;
inflating means attached to the port;
deflating means attached to the inflatable body; and
withdrawal means attached to the inflatable body,
wherein the inflatable body has an inflated configuration and a deflated configuration and wherein, in the inflated configuration, the outer surface is corrugated, fluted, grooved, furrowed or comprises puckers or protrusions of any appropriate shape or dimension, such that, when subject to peristaltic movements, the body in the inflated configuration remains about in place in the rectum or moves upwards due to peristalsis, rather than moving naturally downwards. According to some embodiments, the outer surface comprises any appropriate protrusions that do or do not become inflated upon inflation of the body of the device. According to some embodiments, even if the protrusions themselves do not become inflated, they may change position upon inflation, and become, e.g., more erect when the body is in its inflated configuration, in comparison to their position, in relation to the body of the device in the deflated configuration.

It is noted that in the inflated configuration, any of the bulges from the regular plane of the outer surface, e.g., the inflated puckers or protrusions, or any other elements causing the surface to be corrugated, fluted, grooved, or furrowed, are inflated bulges, such that elements of the outer surface, including any protruding elements, are inflated with gas, plasma or liquid and therefore, are considerably soft or easily pliant. This allows the outer surface to be such that the inflated body remains within a certain height range within the rectum, e.g., about ±1-3 cm from where it was initially positioned, as long as it remains above the dentate line. The combination of the soft material from which the body is prepared together with the inflated elements of the outer surface of the body, allows the body to remain in place or to minimally move upwards or downwards within the rectum. Further, since the body is inflated and may change shape due to external pressure, it may remain in place, or minimally move upwards or downwards therefrom, since the peristalsis movements merely cause the pliable body to change its shape, rather than moving it from its location.

According to some embodiments, the device may further include a stopper, attached to the inflatable body, to prevent unlimited upwards movements of the inflated body of the device. According to some embodiments, any one of the inflating means, deflating means and withdrawal means may include an element that is a stopper for preventing unlimited upwards movements. When the inflatable body is inserted into the rectum, if a stopper is included in the device, the stopper remains on the outside of the patient's anus, and prevents the device from moving with no control too high in the intestine. The stopper may be prepared from any appropriate material, such as silicon, gum, plastic, or any other biocompatible polymer that eases and prevents irritation.

According to some embodiments, any two or all three of the inflating means, deflating means and withdrawal means are incorporated into a combined component.

According to some embodiments, the port has an opened configuration and a closed configuration. According to some embodiments, the port remains in the closed configuration, being transformed into the opened configuration during inflation and/or deflation of the inflatable device. According to some embodiments, when the device is positioned in the rectum, the port is directed downwards, i.e., towards the anus.

According to some embodiments, the deflating means is attached to the port.

According to some embodiments, the inflating means is a tube and a syringe, wherein the tube is attached at one end to the port of inflatable body and at the other end to the syringe. The syringe may be filled with any appropriate gas, plasma or liquid, such as air, water, or any type of gel having a predefined viscosity. According to other embodiments, the inflating means is a tube and a pump, wherein the tube is attached at one end to the port of the inflatable body and at the other end to the pump. The pump may pump any appropriate gas, plasma or liquid. According to some embodiments, the pump is a hand operated pump.

The body of the device may be transformed from its deflated configuration to its inflated configuration by operating the inflating means. For example, by transferring a certain quantity of gas, plasma or liquid from a syringe or pump via a tube into the inflatable body, through the port, the inflatable body may be transformed from its deflated configuration to its inflated configuration. The quantity of gas, plasma or liquid transferred is dependent on the size and volume of the inflatable body and the cross-sectional size of the rectum of the user.

In its inflated configuration, at its widest point, the diameter of the inflatable body is between about 2 cm and about 6 cm. In its inflated configuration, at its widest point, the diameter of the inflatable body is about 2, 3, 4, 5 or 6 cm. It is noted that, throughout this application, the term "inflatable body in its inflated configuration" or the like, may be replaced with the term "inflated body" or the like. Likewise, terms such as "inflatable body in its deflated configuration" or the like, may be replaced with the term "deflated body" or the like.

According to some embodiments, the deflating means is a tube and a syringe, wherein the tube is attached at one end to the port of the inflatable body and at the other end to the syringe. The body of the device may be transformed from its inflated configuration to its deflated configuration by operating the deflating means. For example, the deflating means, e.g., tube connected to a syringe, may be operated by transferring the gas, plasma or liquid from the inflatable body via the port of the inflatable body into the deflating means, e.g., via the tube into the syringe.

According to some embodiments, the inflating means and the deflating means are a combined element, e.g., a tube and a syringe, which may act both as the inflating means and as the deflating means, as required.

According to some embodiments, one element of the inflating means or deflating means remains attached to the port, whereas the other elements of the inflating means or deflating means are disconnected from the device when not in use. For example, if the inflating means and/or the deflating means includes a tube and a syringe, the tube may remain connected to the port at all times, while the syringe it attached to the other end of the tube when it is required to transform the inflatable body from the deflated configuration to the inflated configuration or from the inflated configuration to the deflated configuration.

According to other embodiments, the deflating means is a tether, floss, string, or any other appropriate element, coupled to the port or to any other element in the inflatable body, e.g., the core or any valve/opening/fissure in the core. The inflatable body of the device may be deflated by pulling on the deflating means, such that the port is transformed from its closed configuration to its opened configuration, wherein the gas, plasma or liquid found in the inflatable body is released into the surroundings or such that gas, plasma or liquid are released from any other element the deflating means is coupled to. According to some embodiments, if the deflating means is a tether, floss, string, or any other appropriate element, coupled to the port in the inflatable body, when the device is positioned in the rectum, the port is directed downwards, i.e., towards the anus, such that any matter released from the inflated body will be released towards the anus and from there to the external surroundings or into the deflating means. According to some embodiments, if the deflating means is coupled to another element, that element may be coupled to the port, such that the gas/plasma/liquid is released from that element, to the port and from there to the external surroundings or into the deflating means.

According to some embodiments, the core is located within the inflatable body; however, has an interior separate from the interior of the inflatable body.

The core may provide physical support to the inflatable body. The core may be closed at all ends and may either be filled with any appropriate gas, plasma or liquid that remains therein or may be empty. According to some embodiments, the core is opened at one or both ends. According to some embodiments, the interior of the core is filled with solid matter. According to some embodiments, the core is a solid core, prepared, throughout from the same material as the inflatable body, such that the inflatable body is inflated around a solid core prepared from the same material as the outer surface of the inflatable body. According to some embodiments, the core is prepared from a different, possibly more rigid, material form the outer surface of the inflatable body.

According to some embodiments, the core includes at least one fissure, valve or opening, allowing the passage of material from the interior of the core to the interior of the inflatable device. For example, while a first end of the core may be closed, the second end of the core may incorporate the port such that the gas, plasma or liquid is introduced into the core and from there, via the fissure/valve/opening, is further introduced into the interior of the inflatable body, thereby causing the body to be inflated. Similarly, for example, when the body is deflated, the gas, plasma or liquid may flow form the interior of the body, through the fissure/valve/opening, into the core and then, via the port, to the deflating means or the surroundings.

According to some embodiments, the core may comprise means for absorbing and/or neutralizing liquids and/or gases, such as active charcoal, botanical extracts and the like. Such embodiments of a core may aid in preventing the expulsion of such liquids and/or gases from the intestine.

According to some embodiments, the core is prepared from the same material as the other elements of the inflatable body. According to other embodiments, the core is prepared from a material different from the other elements of the inflatable body. According to some embodiments, at least part of the core is prepared from a material that is more stable or rigid than other elements of the inflatable body.

According to some embodiments, the withdrawal means is a tube, tether, floss, string, or any other appropriate element, having two ends, wherein the first end of the withdrawal means may be coupled to the inflatable body. When the withdrawal means is pulled on by the user, the body may be withdrawn from the rectum. It is noted that the withdrawal means may be operated when the body of the device is in the deflated configuration, such that it is easily withdrawn from the rectum. According to some embodiments, the first end of the withdrawal means is coupled to the inflatable body and the second end of the withdrawal means is coupled to a handle, e.g., a strip or ring that the user may hold onto for withdrawing the device.

According to some embodiments, the withdrawal means and the deflating means are a combined element, e.g., a tube, tether, floss, string or any other appropriate element, which, when pulled on by the user, transforms the port into its opened configuration, thereby releasing the gas, plasma or liquid from the body of the device and transforming the body into its deflated configuration. Further pulling on the combined element withdraws the body of the device from the rectum.

According to some embodiments, the inflating means, deflating means and withdrawal means include at least one combined element, e.g., a tube coupled at one end to the port that may be coupled at the other end to a syringe for inflating/deflating the body and further, acts as the withdrawal means, such that a user may withdraw the body from the rectum by pulling on the tube.

According to one embodiment, the fecal incontinence controlling device of the invention is disposable.

According to this invention, the inflatable body blocks fecal matter, thus controlling incontinence, but allows normal blood flow through all of the surrounding tissues. This ensures that no damage, such as necrosis or gangrene, is caused to the patient due to use of the device of the invention.

The inflatable body is prepared from any biocompatible synthetic or natural material. According to one embodiment, the inflatable is prepared from silicon, silicon polymers, synthetic rubber, such as latex. According to some embodiments, the inflatable body is prepared by dip molding, blown film extrusion, injection molding, press molding or any other appropriate known technique.

According to some embodiments, the device is prepared, such that any two elements thereof may be cast or molded into a single entity. For example, the inflatable body may be cast or molded with at least one element of the inflating means, deflating means and/or withdrawal means permanently attached thereto and may be prepared from the same material. For example, the device may be cast or molded with a tube coupled to the port, such that the tube is permanently attached to the port and may be prepared from the same material, and wherein that tube may be used as part of the inflating means, deflating means and/or withdrawal means. For example, the device may be cast or molded such that the withdrawal means includes a handle that is permanently attached to the withdrawal means and may be prepared from the same material. For example, the device may be cast or molded such that the withdrawal means is coupled at a first end to the port and at a second end to a handle, such that the body of the device, the withdrawal means, including the handle are permanently attached to one another and may be prepared from the same material.

The body of the device may be of any appropriate shape, size and texture, ensuring that it remains in the rectum, above the dentate line, at about 3 cm to about 7 cm, e.g., about 3, 4, 5, 6 or 7 cm, from the anus, blocks the fecal matter from passing it, does not damage the intestine or the rectum, and does not cause pain to the patient. For example, the body of the device may be cylindrical, pear shaped, conical or round. According to certain embodiments, the shape of the body of the device changes with pressure, e.g., as a result of the peristaltic movements of the patient's intestine.

According to some embodiments, the inflatable body may remain above the dentate line, for about 1 to about 12 hours. According to some embodiments, the inflatable body may remain above the dentate line for about 1, 2, 3, 4, 5, 6, 7, 8, 9, 10, 11 or 12 hours.

Further embodiments of the invention are directed to a method for controlling fecal incontinence in a patient, comprising:
inserting an inflatable body into the patient's rectum through the patient's anus, wherein the inflatable body is attached to inflating means, deflating means and withdrawal means, wherein at least a portion of the inflating means, deflating means, and withdrawal means remains outside of the patient's anus;
positioning the inflatable body in the rectum above the dentate line and no more than 7 cm from the anus;
inflating the inflatable body by the inflating means to provide an inflated body;
allowing the inflated body to remain in the rectum above the dentate line until a bowel movement is desired;
deflating the inflated body to provide a deflated body; and
withdrawing the deflated body from the rectum by way of the withdrawal means, thereby allowing the desired bowel movement,
wherein the inflated body has a corrugated, fluted, grooved, or furrowed outer surface or an outer surface that comprises puckers or protrusions, such that, when subject to peristaltic movements, the inflated body remains about in place in the rectum or moves upwards due to peristalsis, rather than moving naturally downwards.

According to some embodiments, the puckers, protrusions or any other elements causing the outer surface to be corrugated, fluted, grooved or furrowed, are inflated together with the inflatable body. According to some embodiments, the puckers, protrusions or any other elements causing the outer surface to be corrugated, fluted, grooved or furrowed, are not inflated, though may change position or configuration in relation to the outer surface when the inflatable body is inflated.

The fecal incontinence device may be used by any patient suffering from fecal incontinence at all grades, including grade 1 (flatus, gases), grade 2a (liquids), grade 2b (liquids and solids) and grade 3 (solids).

According to this invention, the body of the device may be inserted into the patient's intestine by any appropriate means, such as a designated applicator. According to some embodiments, the body of the device may be inserted without an applicator, e.g., if core is rigid enough to allow insertion without an application and e.g., if the head of the body, i.e., the top end thereof, which is inserted first, is rounded to allow easy insertion.

Further embodiments of the invention provide the use of a fecal incontinence controlling device comprising
an inflatable body comprising
a core;
an outer surface; and
a port;
inflating means attached to the port;
deflating means attached to the inflatable body; and
withdrawal means attached to the inflatable body,
wherein the inflatable body has an inflated configuration and a deflated configuration and wherein, in the inflated configuration, the outer surface is corrugated, fluted, grooved, furrowed or comprises puckers or protrusions, such that, when subject to peristaltic movements, the body in the inflated configuration remains about in place in the rectum or moves upwards due to peristalsis, rather than moving naturally downwards.

Reference is now made to FIG. 1A, presenting an embodiment of fecal controlling device 1, in which inflatable body 100 is in the deflated form. As shown, device 1 further includes withdrawal means 110 and inflating means 120 (not fully shown). As detailed herein, the deflating means may be the same element as withdrawal means 110 or as inflating means 120. FIG. 1A further presents core 130, outer surface 140 and port 150. According to the presented embodiment, outer surface 140 comprises protrusions 142. According to the presented embodiments, core 130 comprises port 150 and exhaust valve 134.

As presented in FIG. 1A, withdrawal means 110 may comprise tether 111 and ring 112. According to the presented embodiments, tether 111 is attached to exhaust valve 134 in core 130. It is noted in this respect, that tether 111, or any other element of withdrawal means 110 may be attached to body 100, e.g., to core 130, to outer surface 140, or to port 150, by any appropriate means.

According to some embodiments, inflation means 120 is a syringe filled with any appropriate liquid, plasma or gas. For simplicity, we will refer herein to gas; however, it should be understood that, unless specifically mentioned otherwise, or unless would be understood by a person skilled in the art, any type of liquid or plasma may be used to replace the gas referred to explicitly. Any combination of gas, plasma and/or liquid may be used as well. According to the presented embodiment, inflation means 120 may be filled with a gas (not shown), which may be injected from inflation means 120, via port 150, through core 130 and out of exhaust valve 134 into cavity 160 of body 100. Filling cavity 160 with the gas causes body 100 to transform from its deflated configuration, as shown in FIG. 1A to its inflated configuration, as shown in FIG. 1B.

As shown in FIG. 1B, the position of protrusions 142, in relation to body 100, it erect in the inflated configuration of body 100, in comparison to their position in the deflated form of body 100, as shown in FIG. 1A. It is noted that while in this particular embodiment protrusions 142 themselves are not inflated, it is possible, in other embodiments, that the protrusions themselves become inflated.

In order to transform body 100 from the inflated configuration of FIG. 1B to the deflated configuration of FIG. 1A, deflation means will be implemented. According to some embodiments, withdrawal means 110 may act also as a deflation means, such that when tether 111 is pulled on, e.g., by used holding onto ring 112, gas is allowed to exit from cavity 160 via exhaust valve 134, through core 130, out of port 150, possibly into inflation means 120 (not shown) or possibly into the environment. According to some embodiments, inflation means 120 (not shown in FIG. 1B) may also act as deflation means, such that inflation means 120, which may be a syringe, or a pump, may be attached to port 150 and may, in reverse action to when inflating body 100, draw gas from cavity 160, via exhaust valve 134, through core 130 and out of port 150.

As detailed throughout, when in use, body 100 will be inserted into the rectum when it is in its deflated configuration and, in order to control fecal incontinence, body 100 will be transformed to its inflated configuration. Then, when desired/required to remove body 100 from the rectum, it will be transformed back into its deflated configuration and then removed from the rectum in the deflated configuration.

According to some embodiments, as presented in FIGS. 1A and 1B, device 1 may comprise head 170. Head 170 may be prepared from any appropriate material, e.g., the same material as body 100, the same material as core 130, or a different material. According to some embodiments, head 170 is designed in order to ease the insertion of body 100 into the rectum. According to some embodiments, head 170 includes any appropriate clasping means (not shown) for clasping core 130 to body 100. According to some embodiments, device 1 does not include head 170. According to such embodiments, core 130 and body 100 may be connected at the top by welding, or by being manufactured as one element, e.g., prepared from the same material and manufactured together. According to other embodiments, core 130 and body 100 are connected only at the bottom, or are merely used such that core 130 is inserted into body 100 or into an orifice surrounded by body 100 in such a way that body 100 may be inflated; however, core 130 and body 100 need not be physically connected to one another. According to some embodiments, core 130 and body 100 are connected only at or minimally around exhaust valve 134.

According to some embodiments, body 100 is designed such that core 130 is attached at head 170 to outer surface 140 in order to form cavity 160 around core 130.

Figure 2C:
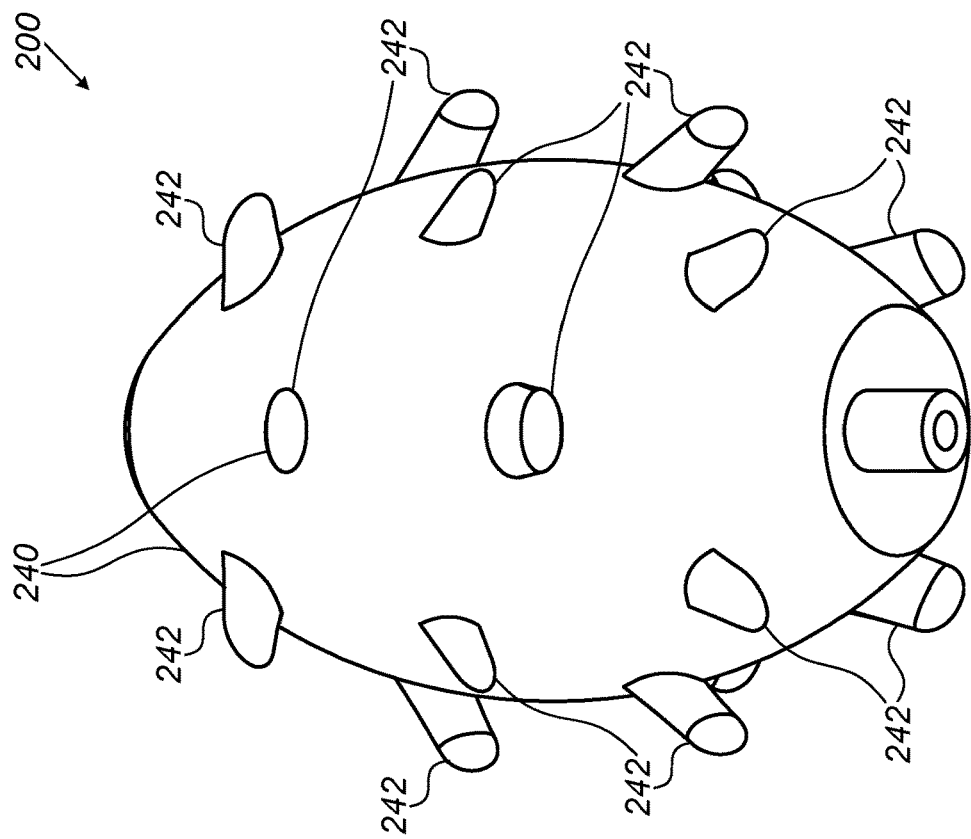
Figure 2B:
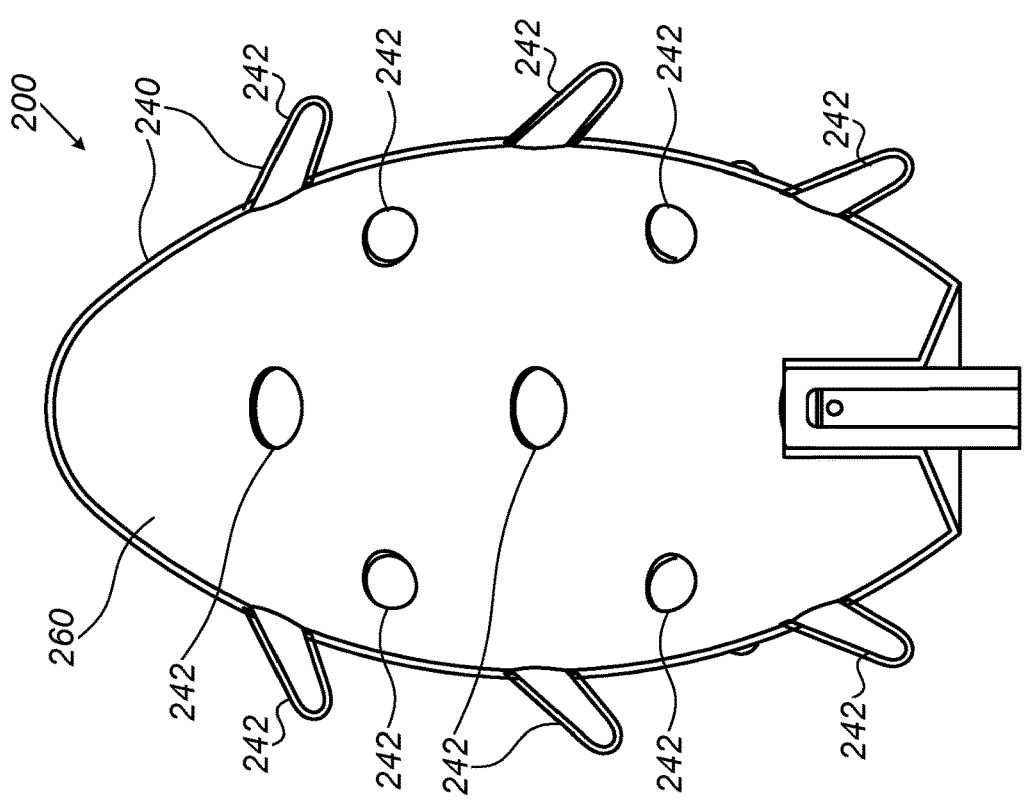

Reference is now made to FIGS. 2A and 2B, respectively presenting a cross section of the deflated and inflated configurations of an embodiment of body 200, in which protrusions 242 are inflated together with body 200. Therefore, as shown in FIG. 2A, each one of protrusions 242 is prepared as part of outer surface 240, such that cavity 260 actually extends into each of protrusions 242. Thus, as presented in FIG. 2B, in the inflated configuration of body 200, protrusions 242 are inflated together with body 200 and are essentially part of cavity 260.

A three dimensional view of body 200 is shown in FIG. 2C, in which it is shown how inflated protrusions 242 protrude from outer surface 240.

According to some embodiments, body 200 may be prepared by any appropriate means, such as dip molding, wherein, according to some embodiments, a single layer may be used in order to form body 200, including outer surface 240 and protrusions 242, which, as essentially extensions of outer surface 240.

It is noted that in FIGS. 2A and 2B, as well as in the following figures, many elements of the device, and even of the body itself, e.g., withdrawal means, inflation means, deflation means, core, etc., are not shown, for simplicity.

Figure 3A:
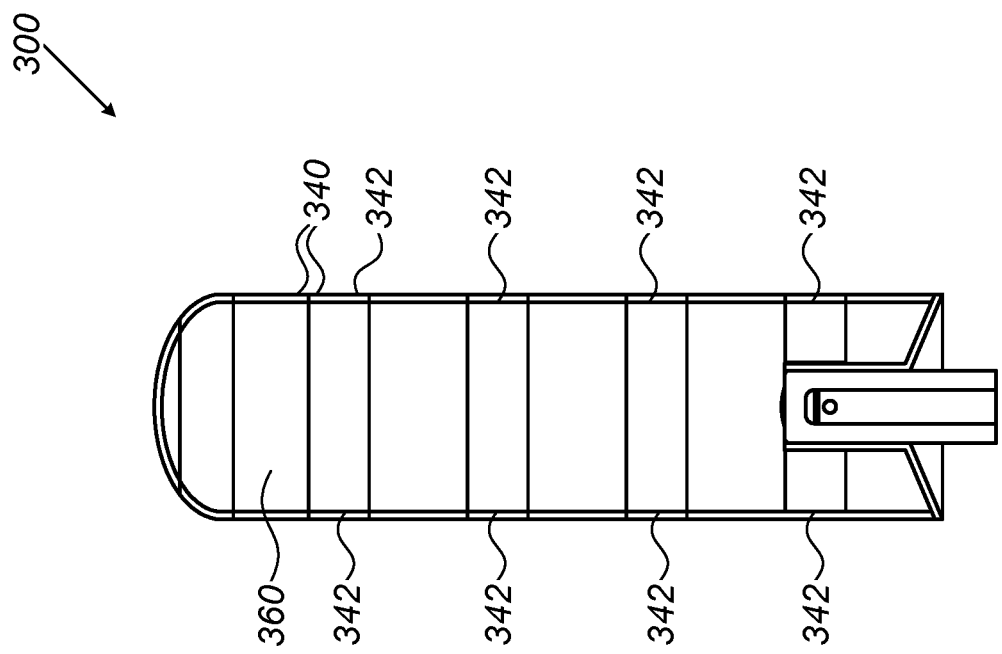
FIGS. 3A and 3B present cross sections of deflated (3A) and inflated (3B) embodiments of bodies of the device comprising inflatable rings and FIG. 3C presents a three dimensional inflated form of the same body with inflatable rings, wherein the body is prepared from one layer.
Figure 3C:
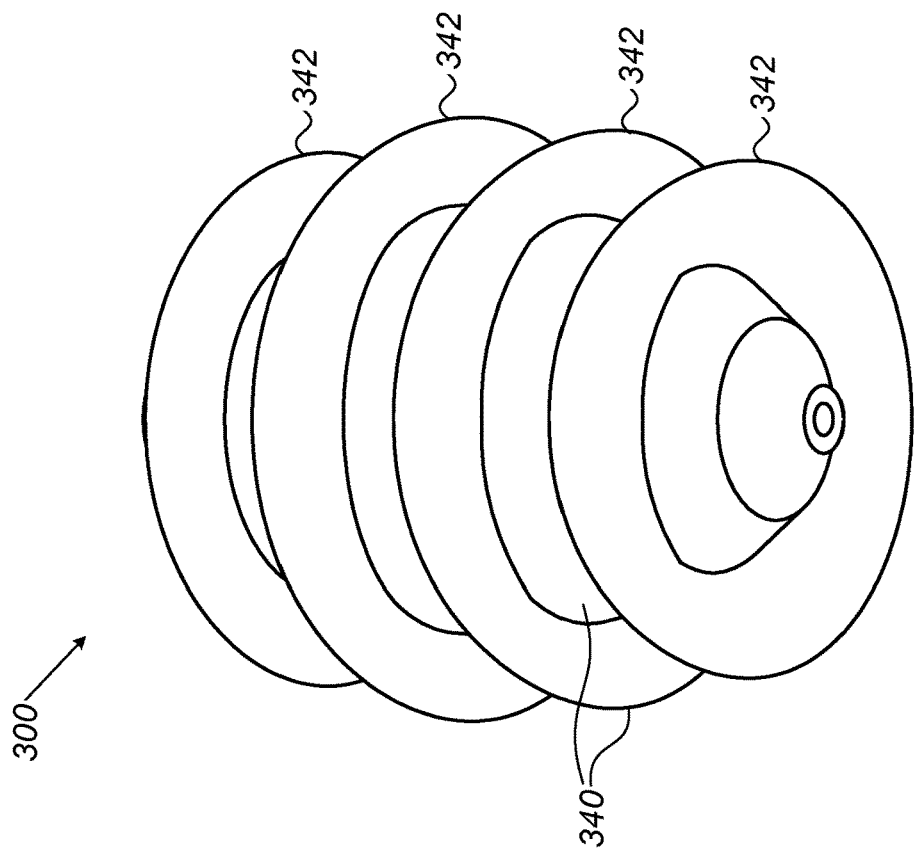
Figure 3B:
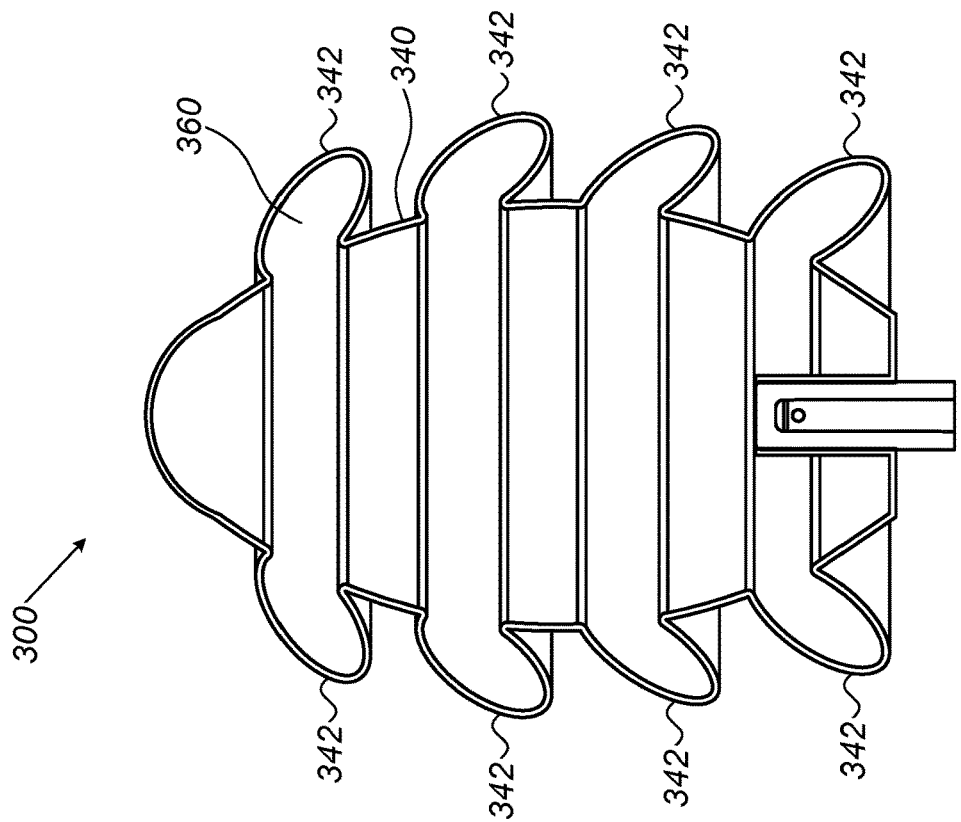

Reference is now made to FIGS. 3A and 3B, presenting a cross section of the deflated and inflated configurations of an embodiment of body 300, in which outer surface 340 comprises inflatable rings 342 that are inflated together with body 300. Therefore, as shown in FIG. 3A, each one of rings 342 is prepared as part of outer surface 340, such that cavity 360 actually extends into each of rings 342. Thus, as presented in FIG. 3B, in the inflated configuration of body 300, rings 342 are inflated together with body 300 and are essentially part of cavity 360. A three dimensional view of body 300 is shown in FIG. 3C, in which it is shown how inflated rings 342 protrude from outer surface 340.

According to some embodiments, body 300 may be prepared by any appropriate means, such as dip molding, wherein, according to some embodiments, a single layer may be used in order to form body 300, including outer surface 340 and rings 342, which, as essentially extensions of outer surface 340.

Figure 4A:
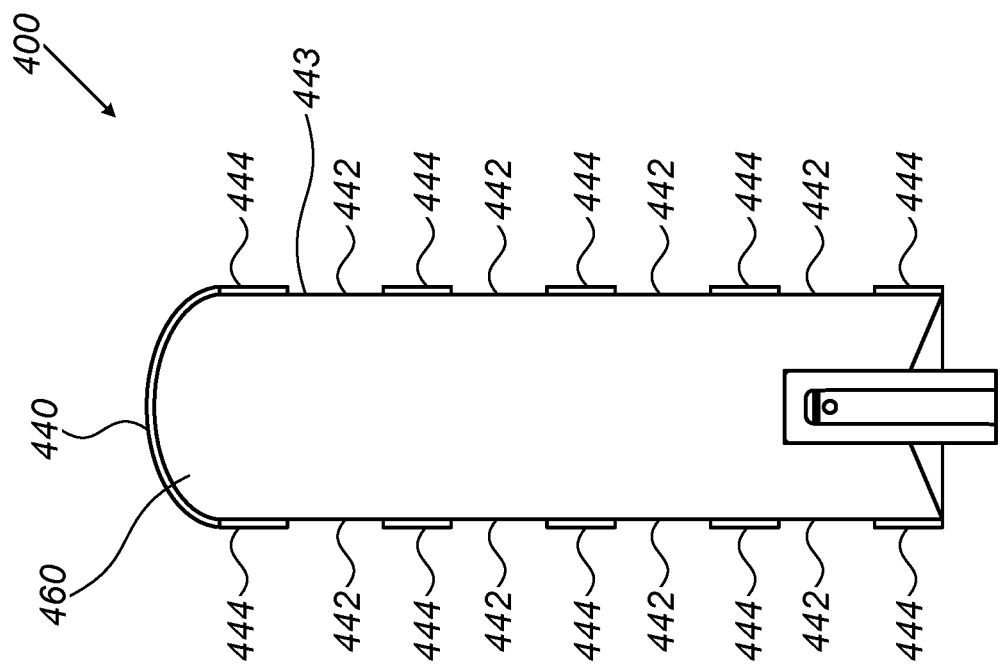
FIGS. 4A and 4B present cross sections of deflated (4A) and inflated (4B) embodiments of bodies of the device comprising inflatable rings and FIG. 4C presents a three dimensional inflated form of the same body with inflatable rings, wherein the body is prepared from two layers.
Figure 4C:
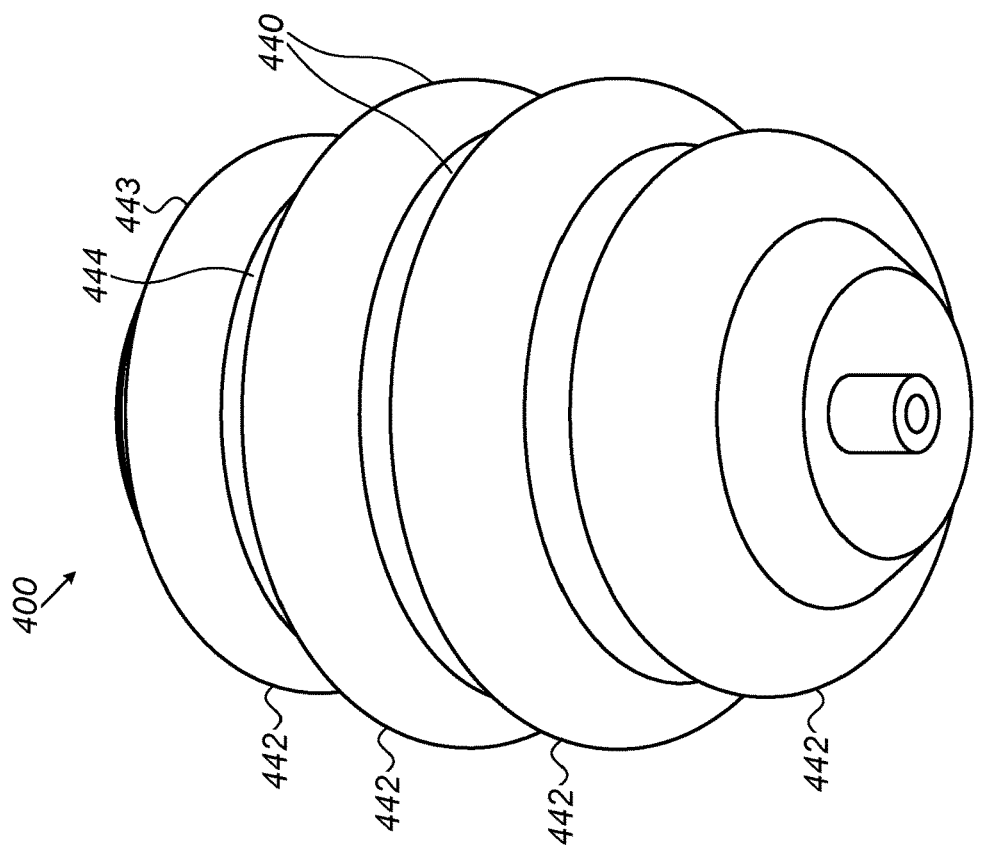
Figure 4B:
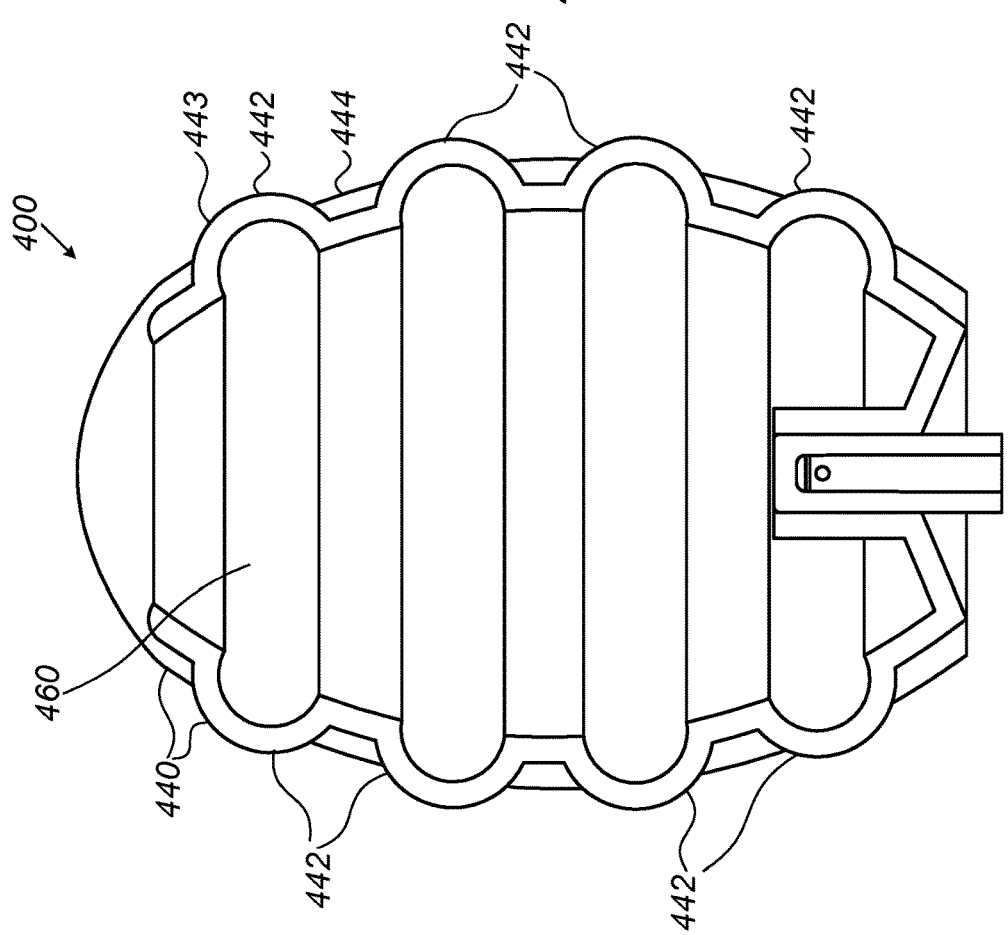

Reference is now made to FIGS. 4A and 4B, presenting a cross section of the deflated and inflated configurations of an embodiment of body 400, in which rings 442 are inflated together with body 400. Therefore, as shown in FIGS. 4A and 4B, outer surface 440 is prepared such that in certain regions, e.g., region 443 (corresponding to the regions of rings 442), outer surface 440 is thin, whereas in other regions, e.g., region 444, outer surface 440 is thick. Therefore, when body 400 is inflated, the thinner regions are more easily inflated than the thicker regions, due to their higher degree of pliability, such that, when inflated, the thinner regions are inflated more than the thicker regions. The shape of the final inflated body is dependent on the shape of the thin and thick regions. FIG. 4B, for Example, presents a cross section of the inflated configuration of body 400 in which rings 442 were formed from the thinner regions, e.g., region 443 and wherein the more rigid regions, e.g., regions 444, did not expand as much, thereby forming rings 442. As shown both in FIGS. 4A and 4B, rings 442 are essentially part of cavity 460.

According to some embodiments, any one of the layers may be between about 0.01 mm and about 0.2 mm. Thus, if two or more layers exist, the overall thickness is the addition of the thickness of the layers at each point. According to some embodiments, each one of the layers may have a thickness different or the same as each one of the other layers.

Figure 5A:
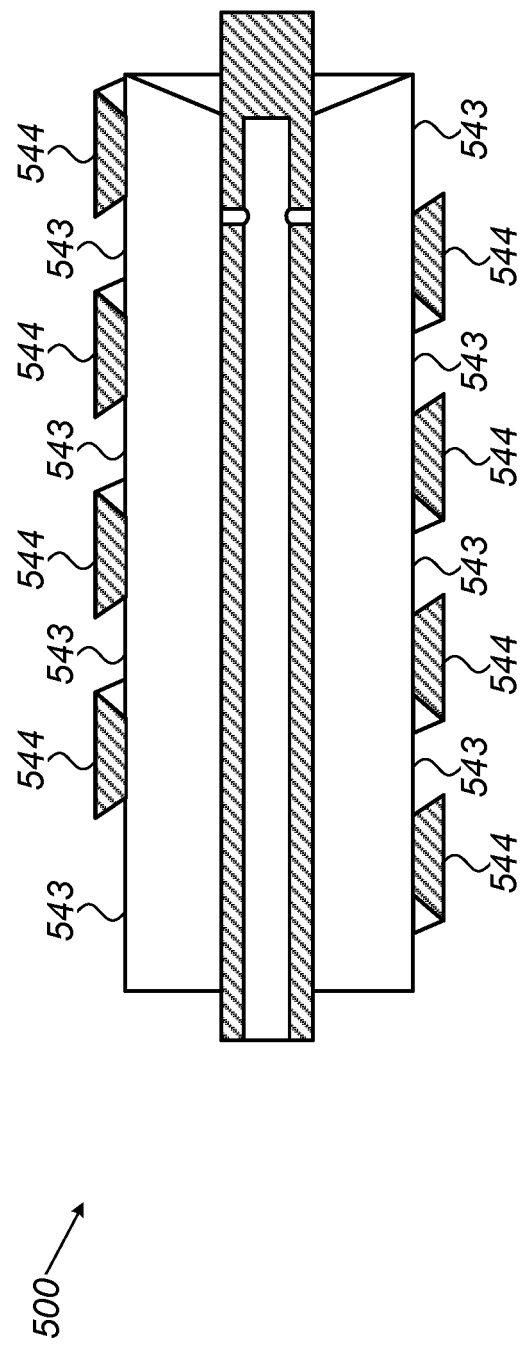
FIGS. 5A and 5B present cross sections of deflated (5A) and inflated (5B) embodiments of bodies of the device comprising an inflatable screw-like ring and FIG. 5C presents a three dimensional inflated form of the same body with an inflatable screw-like ring, wherein the body is prepared from two layers.
Figure 5C:
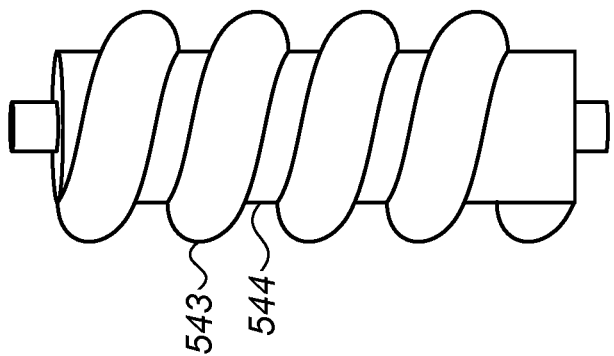
Figure 5B:
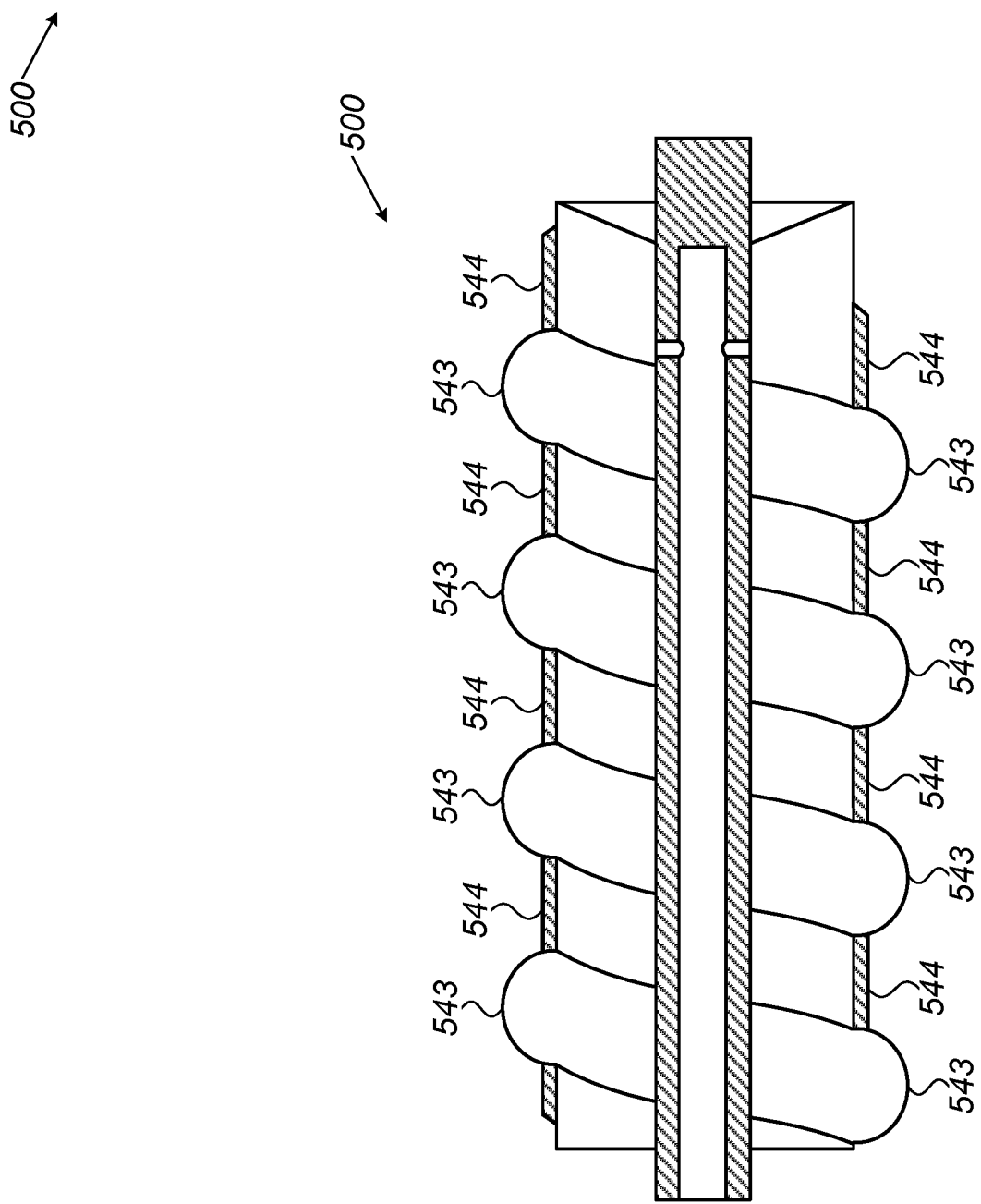

A three dimensional view of body 400 is shown in FIG. 4C, in which it is shown how inflated rings 442 protrude from outer surface 440. It is noted that these rings may be similar in shape to rings 342 in FIG. 3C; however, while body 300 may be prepared from one layer, e.g., by using a mold having a specific shape in order to form the rings, outer surface 440 of body 400 may be prepared from two layers, using a simple cylindrical mold for the first layer, covering the first layer with any appropriate mask in order to form the second layer on only part of the first layer, thereby preparing a body having a first layer and a second, uneven, layer, wherein regions 443 have only the first layer, while regions 444 have both the first layer and the second layer, which allows body 400 to inflate differently in different regions and to therefore form a shape different from a simple cylinder. The second layer may further be prepared by any known means other than a mask, for example, after the first layer is prepared, the second layer may be applied onto the first layer by rotational and transitional movement of the first layer. For example, in order to form a second layer of rings around the first layer (as shown in FIGS. 4A, 4B and 4C), the first layer may be subject to a process in which additional material, e.g., silicon, is injected onto a specific point of the first layer, while rotating the first layer. Once the full rotation is complete, a ring is formed as a second layer on top of the first layer. This may be performed any number of times preparing any number of rings or any desired width. For example, a screw-like ring (as shown in FIGS. 5A, 5B and 5C), the second layer may be applied onto the first layer while the first layer is both rotated and moved forwards, such that the material of the second layer is applied in a screw-like form onto the first layer. It is noted that although this example relates to the use of one or two layers, any number of layers may be used, as detailed herein. It is further noted that any one of the layers may be prepared from the same or different material as any one of the other layers.

Reference is now made to FIGS. 5A, 5B and 5C, presenting a deflated cross section view (FIG. 5A), an inflated cross section view (FIG. 5B) and a three dimensional view of body 500 in which outer surface 540 may be prepared from two layers, as described regarding FIGS. 4A, 4B and 4C. In the embodiment shown in FIGS. 5A, 5B and 5C, a second layer found on a first layer, has a screw shape and therefore, when inflated, as shown in FIGS. 5B and 5C, has a screw shape, double layered, extended ring shape. Particularly, second layered surface 544, turning in screw line form around first layered surface 543, if formed from two layers, while first layered surface 543 is formed from a single layer. Since single layered first layered surface 543 is more pliable, being formed from only a single layer, not a double one, it is more easily inflated and therefore, first layered surface 543 is inflated more than second layered surface 544, which is formed from a double layer, providing the three dimensional body presented in FIG. 5C. As detailed above, the second layer may be formed using any type of appropriate mask.

Figure 6B:
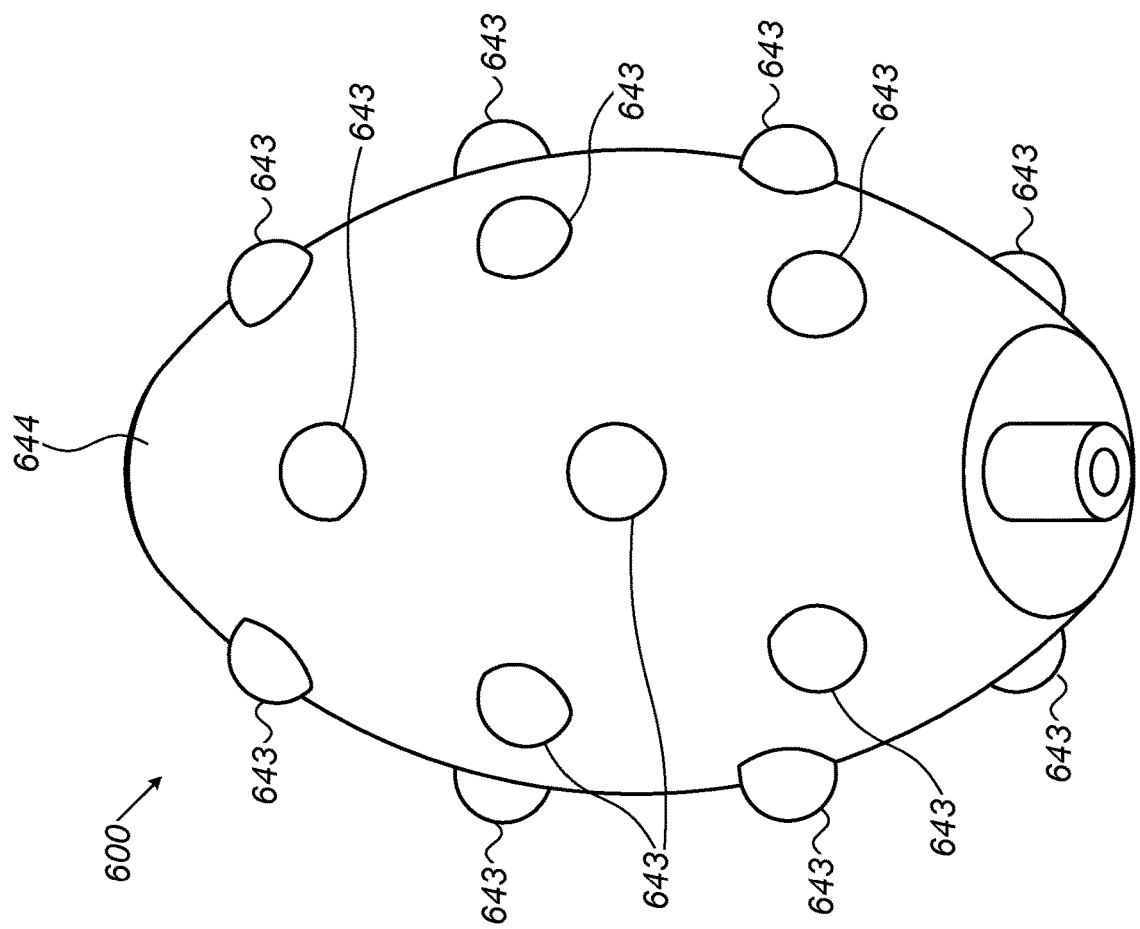
FIGS. 6A and 6B present three-dimensional forms of deflated (6A) and inflated (6B) embodiments of bodies of the device comprising inflatable protrusions, wherein the body is prepared from two layers.
Figure 6A:
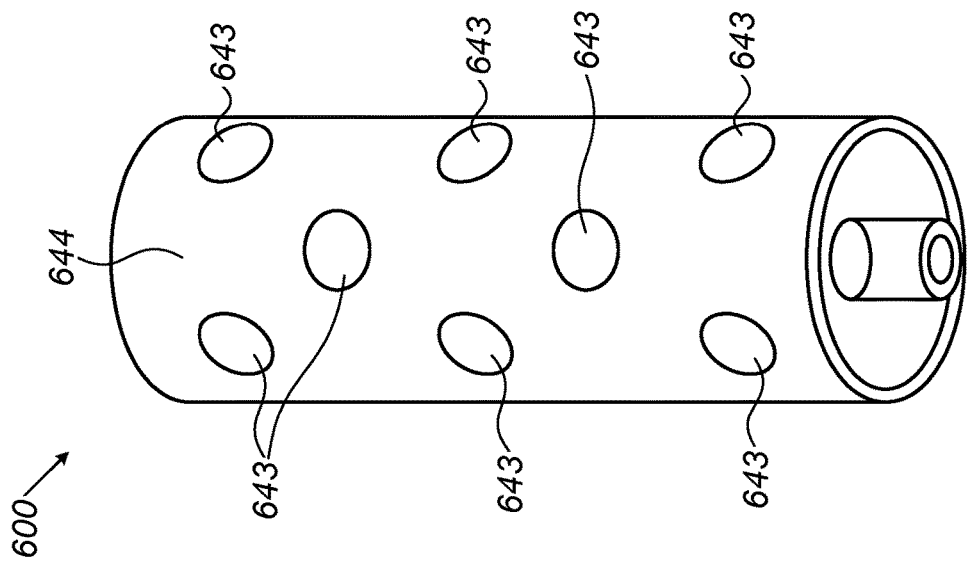

Reference is now made to FIGS. 6A and 6B presenting embodiments of the invention in which the outer surface of body 600 is prepared from first layer 643 and from second layer 644, wherein first layer 643 is single layered and second layer 644 is double layered, such that first layer 643 is more easily inflated than second layer 644. Therefore, as shown in FIG. 6B, when inflated, first layer 643 is inflated more than second layer 644, thereby forming the particular inflated shape of body 600 including inflated protrusions of first layer 643.

It is noted that although a single layer and a double layer are related to above, any similar or equivalent formation of the body of the device is possible, as long as certain portions of the outer surface are prepared to be more easily inflated than other portions of the outer surface. For example, different materials may be used (as long as some portions include materials that are more easily inflated from materials included in other portions of the outer surface), different numbers of layers may be used (as long as some regions have more layers than others). Although generally two regions were discussed above, it is possible, according to some embodiments, that the outer surface be prepared from any number of regions, each having its own inflatability properties, thereby forming any contemplated complex shape for the body of the device, such that when inflated in the rectum, it will not be "flushed" therefrom due to peristalsis.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A fecal incontinence controlling device comprising an inflatable body comprising
   a core;
   an outer surface;
   a port; and
   an exhaust valve;
   inflating means attached to the port;
   deflating means attached to the inflatable body; and
   withdrawal means attached to the exhaust valve of the inflatable body,
   wherein the outer surface comprises inflatable protrusions, wherein any one of the inflating means and the deflating means are configured to be attached and detached from the port; wherein the withdrawal means is configured to be attached and detached from the inflatable body; and
   wherein the inflatable body has an inflated configuration and a deflated configuration and wherein, in the inflated configuration, the inflatable protrusions are inflated, such that, when subject to peristaltic movements, the body in the inflated configuration remains about in place in the rectum or moves upwards due to peristalsis, rather than moving naturally downwards.

2. The device according to claim 1, wherein the outer surface is prepared from a single layer.

3. The device according to claim 1, wherein the outer surface comprises more than one region, wherein each region is prepared from a different number of layers.

4. The device according to claim 1, wherein the withdrawal means is a tether connected at one end to the inflatable body and, optionally, at the other end to a handle.

5. The device according to claim 1, wherein the inflating means is a syringe.

6. The device according to claim 1, wherein the deflating means is a syringe.

7. The device according to claim 1, wherein the deflating means is a tether connected at one end to the inflatable body and, optionally, at the other end to a handle.

8. The device according to claim 1, wherein any two or all of the withdrawal means, inflating means and deflating means are incorporated into a single element.

9. The device according to claim 1, wherein the deflating means is attached to the port.

10. A method for controlling fecal incontinence in a patient, said method comprising:
    inserting an inflatable body in a deflated configuration into the rectum until reaching a position above the dentate line, wherein said inflatable body comprises a core, an outer surface, a port and an exhaust valve, wherein the outer surface comprises inflatable protrusions;
    inflating the inflatable body by inflating means attached to the port thereby transforming the inflatable body to the inflated configuration to provide an inflated body, wherein, in the inflated configuration, the inflatable protrusions are inflated;
    detaching the inflating means from the port; and, when desired or required to remove the inflated body from the rectum, if not already attached, attaching deflating means to the inflated body,
    deflating the inflated body by the deflating means, thereby transforming the inflatable body to the deflated configuration to provide a deflated body, wherein, in the deflated configuration, the inflatable protrusions are deflated;
    if not already attached, attaching withdrawal means to the exhaust valve of the deflated body;
    withdrawing the deflated body from the rectum by withdrawal means.

11. The method according to claim 10, wherein the inflatable body is inflated with air.

12. The method according to claim 10, wherein the inflating means is a syringe.

13. The method according to claim 10, wherein the deflating means is a syringe.

14. The method according to claim 10, wherein the deflating means is a tether, which, when pulled on, causes the inflated body to be transformed to its deflated configuration.

15. The method according to claim 10, wherein the withdrawal means is a tether, which, when pulled on, withdraws the deflated body from the rectum.

16. The method according to claim 15, wherein the withdrawal means further includes a handle attached to said tether.

* * * * *